United States Patent
Smith et al.

(10) Patent No.: US 8,558,702 B2
(45) Date of Patent: Oct. 15, 2013

(54) APPARATUS AND METHOD FOR PREVENTING PRESSURE INJURIES AND CIRCULATORY PROBLEMS IN SEDENTARY PATIENTS

(76) Inventors: Kyle B. Smith, Dallas, TX (US); Kamal Mamdani, Dallas, TX (US); Sahit V. Dendekuri, Frisco, TX (US); Joseph G. Vettoretti, Dallas, TX (US); Ruoming Fan, Dallas, TX (US); Dalton A. Glenn, Rowlett, TX (US)

( * ) Notice: Subject to any disclaimer, the term of this patent is extended or adjusted under 35 U.S.C. 154(b) by 178 days.

(21) Appl. No.: 12/960,295

(22) Filed: Dec. 3, 2010

(65) Prior Publication Data

US 2012/0139732 A1   Jun. 7, 2012

(51) Int. Cl.
*G08B 23/00* (2006.01)
(52) U.S. Cl.
USPC ...................................... 340/573.1; 340/573.7
(58) Field of Classification Search
USPC ................................ 340/573.1, 573.7, 539.12
See application file for complete search history.

(56) References Cited

U.S. PATENT DOCUMENTS

| | | | |
|---|---|---|---|
| 4,554,930 A | 11/1985 | Kress | |
| 7,504,955 B2 | 3/2009 | Overturf | |
| 2004/0046668 A1* | 3/2004 | Smith et al. | 340/573.7 |
| 2005/0004476 A1* | 1/2005 | Payvar et al. | 600/481 |
| 2009/0009320 A1* | 1/2009 | O'Connor et al. | 340/539.12 |

* cited by examiner

*Primary Examiner* — Shirley Lu
(74) *Attorney, Agent, or Firm* — Bell Nunnally & Martin, LLP; Craig J. Cox

(57) ABSTRACT

A warning device for the prevention of pressure sores and circulation problems from prolonged inactivity includes a sensor positioned in a pad to detect the weight of a user on the pad. A sitting timer measures the amount of time the user has continuously sat on the pad, and an alarm activated by the warning device when the user has continuously sat on the pad in excess of a first predetermined limit, wherein the alarm includes a visual alarm mechanism, an auditory alarm mechanism, and a sensory alarm mechanism. A standing timer is started when the user's weight is removed from the pad and measuring the amount of time the user has been off of the pad. The alarm is reactivated if the sensor detects the user's weight reapplied to the pad before the standing timer has expired.

8 Claims, 2 Drawing Sheets

APPARATUS AND METHOD FOR PREVENTING PRESSURE INJURIES AND CIRCULATORY PROBLEMS IN SEDENTARY PATIENTS

TECHNICAL FIELD OF THE INVENTION

The present invention relates generally to an apparatus and method for the prevention of pressure sores and circulation problems from prolonged inactivity. More particularly, the present application involves a reminder that alerts an individual of the need to get up and move about to avoid the formation of pressure sores and circulatory issues.

BACKGROUND OF THE INVENTION

Prolonged sitting, reclining or laying in the same position is known to present issues that can be harmful, such as bedsores, ulcers and issues relating to blood circulation, such as blood clots. In many instances, however, people are subjected to prolonged periods of inactivity due to age, infirmity, illness, surgery or other conditions. People who may be prone to these prolonged periods in a single position, such as sitting in a wheel chair or laying in a hospital bed may need to be alerted after a certain amount of time to stand or move about to prevent the formation of bedsores, ulcers, blood clots or similar issues.

There have been previous attempts to develop devices to warn patients of prolonged periods without movement. One such device is described in U.S. Pat. No. 4,554,930 issued on Nov. 26, 1985 to Kress. Kress measures the pressure on a patient's skin and then warns the patient before the pressure has been applied long enough to cause damage to the skin. Another device is described in U.S. Pat. No. 7,504,955 issued on Mar. 17, 2009 to Overturf. It also detects the pressure applied by a user to a particular area and warns the user when the pressure has been applied for a predetermined amount of time. Overturf further includes a mechanism to alter the inclination of the patient, thus changing the relative pressure points.

These and other prior art devices suffer from a number of deficiencies. First, in order to ensure that potential injuries or issues are avoided from prolonged periods of pressure, the patient or user needs to keep the pressure removed from the affected area for a minimum amount of time. Reapplication of the pressure too soon to the affected area can have deleterious affects. None of the prior art devices monitor the length of time the patient or user has stayed off of the relevant pressure points and none are able to warn the patient if they sit or lay down too quickly after getting up. Further, the prior art devices are unable to account for patients who get up before being warned. The prior art devices work on fixed cycles and are unable to adjust their operation to account for patients moving before they have been warned by the device.

BRIEF SUMMARY OF THE INVENTION

To overcome the deficiencies of the prior art, a warning device is described that in preferred embodiments includes a sensor positioned to detect the weight of a user in an area of interest. A first timer measures the amount of time the user has been positioned in the area of interest. An alarm is activated by the warning device when the user has been positioned in the area of interest in excess of a first predetermined limit, and a second timer measuring the amount of time the user has been out of the area of interest, wherein the alarm is reactivated if the sensor detects weight in the area of interest before a second predetermined limit has been reached by the second timer.

In an alternate embodiment, a method for warning a user to protect against prolonged sitting is described. The method includes detecting the presence of the user when the user's bodyweight is applied to an area of interest, starting a sitting timer, and monitoring the area of interest to detect when the user's bodyweight is removed from the area of interest. An alarm is activated in the event the user has not moved before the expiration of a sitting timer, and a standing timer is started when the user has moved from the area of interest. The alarm is reactivated if the user's bodyweight is reapplied to the area of interest before the expiration of a standing timer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Many elderly or people with medical issues have a tendency to remain in the same position for prolonged periods because movement is made difficult by the age or medical conditions. Sitting or laying in the same position for prolonged periods can lead to additional issues such as bedsores, ulcers, circulatory problems and blood clots. One way to prevent these problems is to get those that are able to stand and move periodically so that pressure is not applied to the same region for extended periods and blood circulation is promoted.

The present invention describes a system and method for preventing the problems associated with patients who are susceptible to spending long periods in sitting or laying positions. Embodiments of the present invention include a cushion or mat that detects when a person sits or lays on it. Upon detection, the device of the present invention activates a timer that warns the patient when they have been sitting or laying too long. The cushion or mat of the present invention can be made to accommodate any particular position such as sitting, reclining, or laying down or any piece of equipment or furniture, such as a chair, wheelchair, bed, or sofa.

Figure 1:
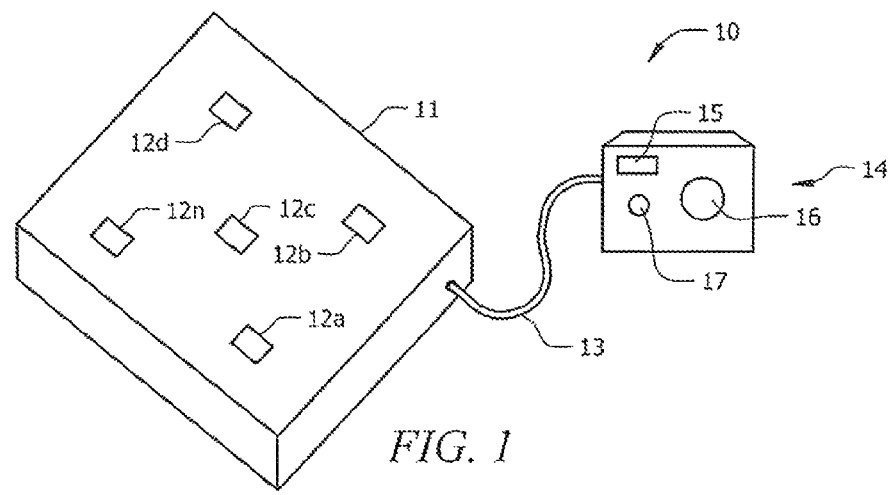
FIG. 1 is a perspective view of an embodiment of a cushion according to the present invention.

Referring now to FIG. 1, an embodiment of a warning device 10 according to the concepts of the present invention is described. Warning device 10 includes cushion 11. As described, cushion 11 can be chosen for any particular application and can be made of any suitable material. Cushion 11 includes one or more sensors 12a, 12b, 12c, 12d through 12n. The sensors detect the presence of someone sitting or laying on cushion 11 and can be any type of suitable sensor or switch and located relative to the cushion anyplace that is appropriate for proper operation. For example, cushion 11 may be an inflatable air cushion, in which case the sensors may be pressure sensors that measure the air pressure in the cushion and detect the presence of a person by the increase in air pressure when weight is applied. Other configurations can include foam cushions, rubber mats, pillows or the like. The sensors can be switches, such as bump switches or any other type of sensor or switch that will detect the presence of weight or pressure on the cushion.

Sensors 12a through 12n and cushion 11 are connected to a control module 14. In the embodiment of FIG. 1, control module 14 is shown external to cushion 11 and operatively connected by cord or wires 13, but it would be apparent to anyone skilled in the art that control module 14 can be located anywhere relative to cushion 11 including being incorporated inside cushion 11. Further, the connection could be integral, wired or wireless without departing from the scope of the present invention.

Control module 14 includes the logic to control warning device 10 and may include one or more alarms, such as a visual alarm 17 which may be a flashing light, or an auditory alarm, using speaker 16 to warn the user. Other types of alarms are well within the scope of the present invention, such as a sensory alarm, which could be a vibrator such as is used in mobile phones. Control module 14 may also include an on/off switch 15. Power for the warning device 10 could be supplied by batteries or by plugging warning device 10 into an outlet.

Figure 2:
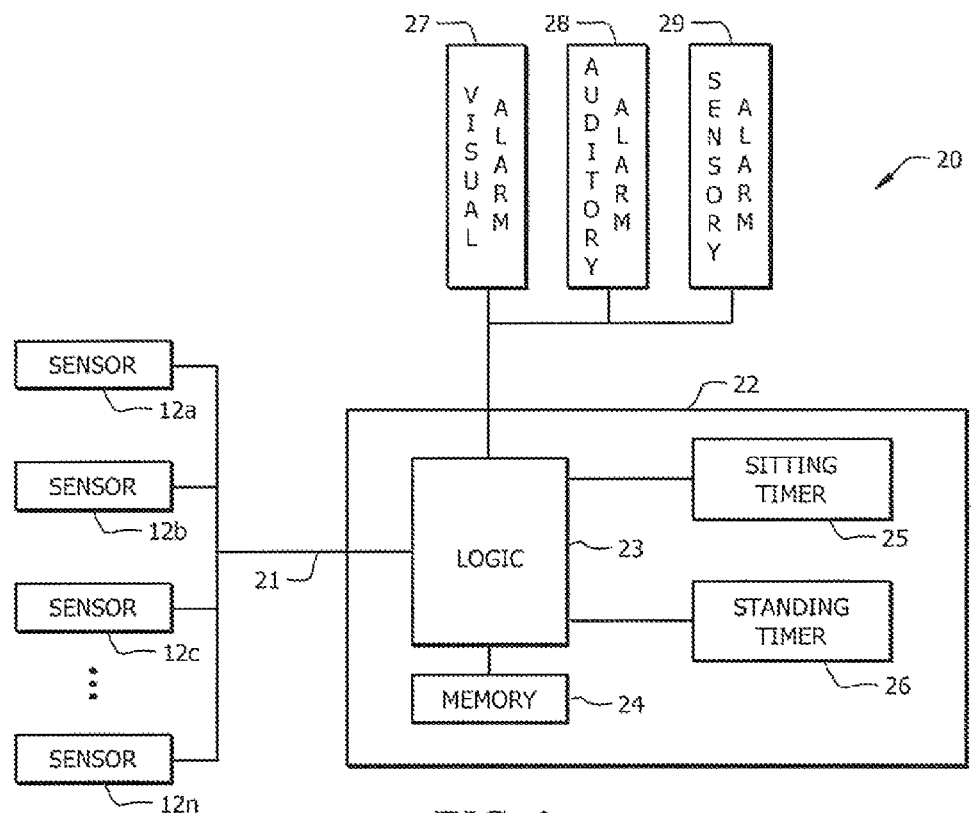
FIG. 2 is a simplified block diagram of an embodiment of circuit according to the present invention.

Referring now to FIG. 2, an embodiment of the electronics used to control warning device 10 is described. Electronics 20 include one or more sensors 12a, 12b, 12c, through 12n, used to detect the presence of a person on the cushion through weight or pressure, as described above. The sensors are connected to controller 22 which includes the program and/or logic for implementing the warning program. Controller 22 can be implemented either on a microprocessor or other programmable device or can be implemented with discrete logic elements.

Controller 22 includes logic 23 which monitors and controls the sensors and other elements of warning device 10. Logic 23 is connected to at least two timers used to monitor the user's activities. A sitting timer 25 is activated when the user sits or lays on the cushion as detected by sensors 12a through 12n. Sitting timer 25 is monitored by the logic, and when logic 23 detects that it has reached a predetermined limit, logic 23 actives an alarm to warn the user that they should move or stand to relieve pressure points and promote blood circulation. A standing timer is activated after the logic detects that the person has stood up and measures the amount of time the user is off of the cushion. If the user sits back down before the standing timer has reached a predetermined threshold, the logic again activates the user to warn them that they have not been moving or standing for long enough to relieve the skin pressure or to promote circulation.

The alarms used by Warning device 10 can be any mechanism sufficient to gain the attention of the user. In a preferred embodiment, warning device 10 employs multiple alarms of different types to ensure the user is alerted. The different types of alarms work with different senses of the user to make sure that the warning is understood. For example, in the embodiment of FIG. 2, the warning device 10 uses a visual alarm 27, which can be one or more lights, such as LEDs, and those lights may be made to flash or pulse. The device also uses an auditory alarm 28, such as a speaker playing an alarm or a prerecorded message to the user. The device may also included a sensory alarm 29 that is capable of being felt by the user, such as a vibrator. The use of multiple, different alarms also allows the warning device to be used by patients that may have other disabilities such as blindness, deafness, or neuropathy. The alarms may be located in the cushion 11, control module 14 or any other location that serves to alert the user.

Logic 23 may be connected to a memory 24 which can be used to hold patient specific parameters used to vary or adjust the operation of warning device 10. For example, a younger person, or a person with only a temporary disability may not need to move as often as an older or more permanently disabled person. Therefore, the warning device need not warn the person to move or stand up as often and that person may not need to be off the cushion for as long a period and may otherwise be necessary.

Figure 3:
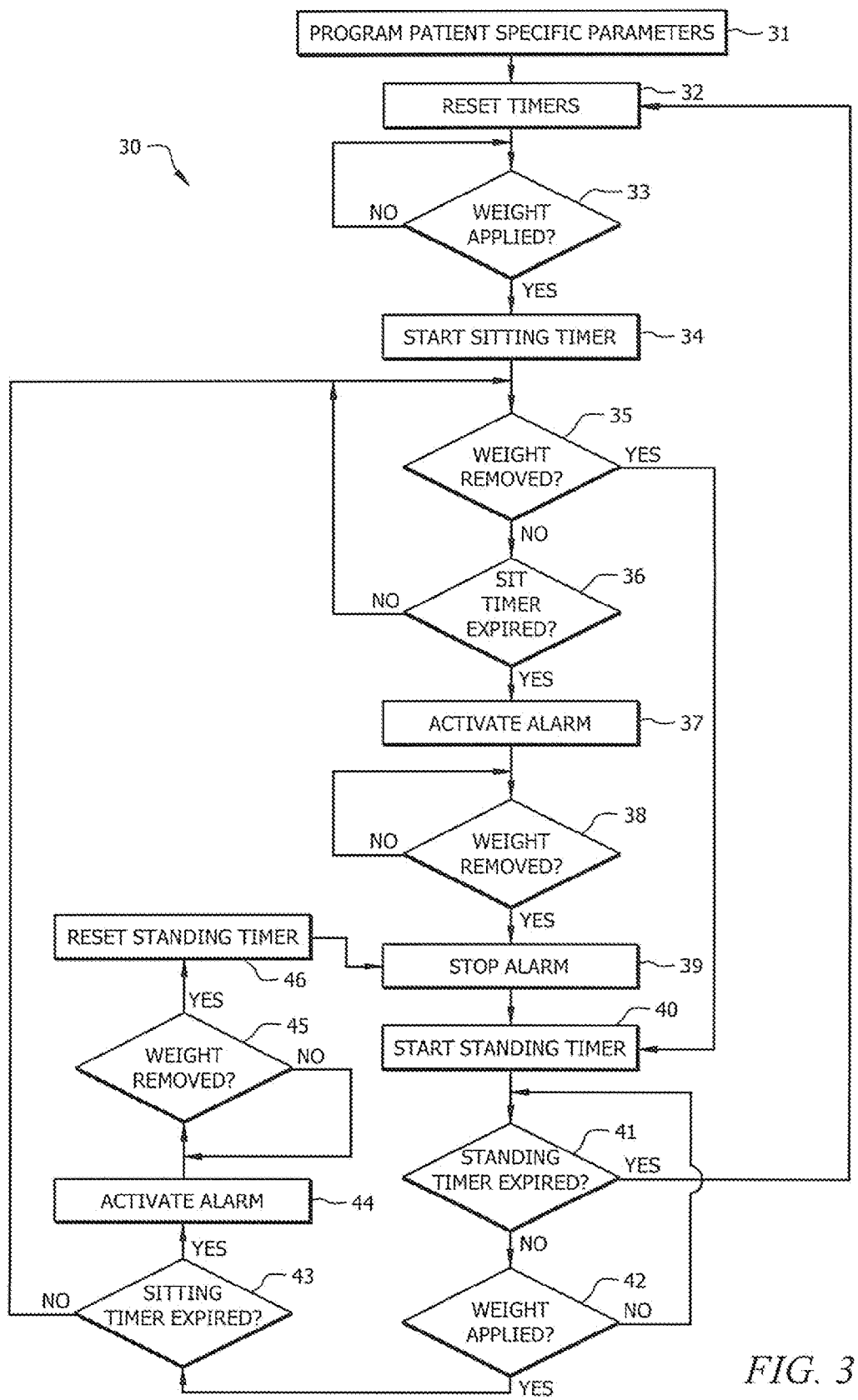
FIG. 3 is a flow chart illustrating a preferred method of operating a warning device in accordance with the present invention.

Referring now to FIG. 3, an embodiment of a method according to the present invention is described. Method 30 is a preferred method for operating a warning device such as that described in FIGS. 1 and 2. Method 30 begins with the entry of any patient specific parameters 31. These parameters can be used to set the maximum sitting time and minimum standing time based on any relevant factors. Next, the timers are reset or initialized 32. The method then waits until the presence of a user is detected 33, such as by weight being applied to cushion 11 from FIG. 1, thereby activating one or more sensors 12a through 12n.

Once the presence of a user is detected, the sitting timer is started 34. The method then monitors the presence of the user 35. If the user stands up or removes his or her weight from the cushion before the sitting timer reaches a predetermined limit, the method proceeds to start the standing timer 40, as will be discussed in greater detail below. If the user has not stood up, the sitting timer is monitored 36. If the sitting timer reaches a predetermined time without the user standing, the alarm mechanism is activated 37. Once the alarm is activated, the method again monitors to see if the patient has stood or removed pressure from the cushion 38. Once the user stands, the alarm is turned off 39, and the standing timer is started 40.

The method then monitors to see, relative to the state of the standing timer 41, when pressure is reapplied to the cushion by the patient 42. If the standing timer expires before the patient sits down again, the method returns to the resetting of the timers 32 and waits for the user to sit 33. If, however, the user sits down again before the standing timer is expired, the method checks to see if the sitting timer had previously expired 43. If not, the method returns to the initial monitoring condition 35 after the patient sits down. If the sitting timer has already expired, the alarm is reactivated 44, warning the user that they have not stood for enough time. The method then monitors to determine when the patient stands up again 45, and when the patient stands up, the standing timer is reset 46, the alarm is deactivated 39 and the standing timer is restarted. The method then continues as previously described.

While a specific embodiment of a method has been described, those skilled in the art will appreciate that variations, additions and subtractions can be made without departing from the scope of the concepts described herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A patient warning device comprising:
    a pad shaped to be placed in an area where a patient spends a significant amount of time;
    multiple sensors positioned to detect the weight of a user on the pad;
    a first timer measuring the amount of time the user has been positioned on the pad;
    an alarm to alert the patient, the alarm activated by the warning device when the user has been positioned in the area of interest in excess of a first predetermined limit, wherein the alarm includes a visual alarm, an auditory alarm and a vibrating alarm; and
    a second timer measuring the amount of time the user has been off of the pad, wherein the alarm is reactivated if the sensor detects weight on the pad before a second predetermined limit has been reached by the second timer.

2. The device of claim 1 wherein the pad is adapted to be sat on by the user.

3. The device of claim 1 wherein the pad is adapted to be laid on by the user.

4. The device of claim 1 wherein the first timer resets whenever the user has been out of the area of interest for the duration of the second predetermined limit measured by the second timer.

5. A warning device to warn a sedentary patient when the patient has been sitting for too long, the warning device comprising:
    a pad shaped to be positioned to be sat on by the sedentary patient;
    a sensor positioned in the pad to detect the weight of the sedentary patient on the pad;
    a sitting timer measuring the amount of time the sedentary patient has continuously sat on the pad;
    an alarm activated by the warning device when the sedentary patient has continuously sat on the pad in excess of a first predetermined limit, wherein the alarm includes a visual alarm mechanism, an auditory alarm mechanism, and a sensory alarm mechanism sufficient to warn the patient; and
    a standing timer started when the user's weight is removed from the pad and measuring the amount of time the user has been off of the pad, wherein the alarm is reactivated if the sensor detects the user's weight reapplied to the pad before the standing timer has expired;
    wherein the sitting timer resets anytime the user's weight has been off the pad at least until the standing timer has expired.

6. The warning device of claim 5 wherein the warning device is contained entirely within the pad.

7. The warning device of claim 5 wherein the standing timer, the sitting timer, and the alarm are external to the pad.

8. The warning device of claim 5 wherein the pad is adapted to be placed in a wheelchair.

* * * * *